US009046515B2

(12) United States Patent
Matsumoto et al.

(10) Patent No.: US 9,046,515 B2
(45) Date of Patent: Jun. 2, 2015

(54) POLYMER COMPOUND FOR MEDICAL MATERIAL, AND BIOCHIP SUBSTRATE USING THE POLYMER COMPOUND

(75) Inventors: Takayuki Matsumoto, Tokyo (JP); Sumio Shibahara, Tokyo (JP); Sohei Funaoka, Tokyo (JP); Daisuke Masuda, Tokyo (JP)

(73) Assignee: SUMITOMO BAKELITE COMPANY, LTD., Tokyo (JP)

( * ) Notice: Subject to any disclaimer, the term of this patent is extended or adjusted under 35 U.S.C. 154(b) by 1040 days.

(21) Appl. No.: 11/920,560

(22) PCT Filed: May 18, 2006

(86) PCT No.: PCT/JP2006/309920
§ 371 (c)(1),
(2), (4) Date: Feb. 9, 2009

(87) PCT Pub. No.: WO2006/123737
PCT Pub. Date: Nov. 23, 2006

(65) Prior Publication Data
US 2009/0176298 A1    Jul. 9, 2009

(30) Foreign Application Priority Data

May 19, 2005  (JP) ................................. 2005-146122
Jan. 10, 2006  (JP) ................................. 2006-002015

(51) Int. Cl.
| *B05D 3/00* | (2006.01) |
| *C12M 1/00* | (2006.01) |
| *G01N 33/543* | (2006.01) |
| *C08F 2/38* | (2006.01) |
| *C08F 290/06* | (2006.01) |
| *C08G 65/332* | (2006.01) |
| *C08G 65/333* | (2006.01) |
| *C08G 65/336* | (2006.01) |
| *C09D 133/00* | (2006.01) |
| *C09D 155/00* | (2006.01) |
| *C08F 220/36* | (2006.01) |
| *G01N 35/00* | (2006.01) |

(52) U.S. Cl.
CPC ............ *G01N 33/54393* (2013.01); *C08F 2/38* (2013.01); *C08F 220/36* (2013.01); *C08F 290/06* (2013.01); *C08F 290/062* (2013.01); *C08G 65/3322* (2013.01); *C08G 65/33379* (2013.01); *C08G 65/33396* (2013.01); *C08G 65/336* (2013.01); *C08L 2203/02* (2013.01); *C09D 133/00* (2013.01); *C09D 155/005* (2013.01); *G01N 2035/00158* (2013.01)

(58) Field of Classification Search
None
See application file for complete search history.

(56) References Cited

U.S. PATENT DOCUMENTS

| 5,086,143 | A | 2/1992 | Sutton et al. |
| 5,200,315 | A | 4/1993 | Sutton et al. |
| 5,330,891 | A | 7/1994 | Sutton et al. |
| 6,713,533 | B1 | 3/2004 | Panzner |
| 7,001,673 | B2 | 2/2006 | Yamasaki et al. |
| 8,088,340 | B2 * | 1/2012 | Matsumoto et al. ........... 422/420 |
| 2002/0043499 | A1 * | 4/2002 | Hammen et al. ............... 210/656 |
| 2002/0131246 | A1 * | 9/2002 | Hawker et al. ................. 361/750 |
| 2002/0134266 | A1 | 9/2002 | Yamasaki et al. |
| 2003/0124371 | A1 * | 7/2003 | Um et al. ....................... 428/522 |
| 2004/0077797 | A1 * | 4/2004 | Asgarzadeh et al. .......... 525/404 |
| 2005/0100675 | A1 * | 5/2005 | Mao et al. ...................... 427/384 |
| 2005/0176003 | A1 * | 8/2005 | Yokoyama et al. ............... 435/6 |
| 2006/0073414 | A1 | 4/2006 | Yamasaki et al. |

FOREIGN PATENT DOCUMENTS

| EP | 0 468 584 A2 | 1/1992 |
| EP | 0 468 585 A2 | 1/2002 |
| EP | 1 226 976 A1 | 7/2002 |
| JP | 63-112605 | 5/1988 |
| JP | 2-108699 | 4/1990 |
| JP | 6-93035 | 4/1994 |
| JP | 6-313009 | 11/1994 |
| JP | 7-3171 | 1/1995 |
| JP | 8-143678 | 6/1996 |
| JP | 9-28790 | 2/1997 |
| JP | 2001-116750 | 4/2001 |
| JP | 2001-261740 | 9/2001 |
| JP | 2001-316405 | 11/2001 |

(Continued)

OTHER PUBLICATIONS

Yadavalli et al, Sensors and Actuators B, vol. 97, pp. 290-297 (2004).*
The Nektar Catalog (2005-2006) [retrieved on Feb. 2, 2011]. Retrieved from the Internet: <URL: www.sejinbio.co.kr/Catalogue/Nektar>.*
The defintion of PEGDA from glycosan.com [retrieved on Feb. 10, 2011]. Retrieved from the Internet: <URL: www.glycosan.com/peg_products/pegda.html >.*
Supplementary European Search Report for Application No. EP 06 74 6605 dated Nov. 23, 2010.
"Practical Manual of DNA Microarray", Dec. 1, 2000, Fumiaki Kasai (Publisher), Yodosha Co., Ltd. (Published by), p. 57, Lines 5-11.
Japanese Office Action issued on Aug. 14, 2012 for Application No. 2007-516336.
Japanese Office Action issued on Apr. 24, 2012 for Application No. 2007-516336.

*Primary Examiner* — Robert T Crow
(74) *Attorney, Agent, or Firm* — Smith, Gambrell & Russell, LLP

(57) ABSTRACT

A main object of the invention is to provide a polymer compound for medicine which has an excellent capability of fixing a biologically active substance and has such chemical/physical stability that the compound is less dissolved or deteriorated in a washing step, in particular, which can be suitably applied to a plastic substrate surface.
The invention provides a polymer compound for medical material which is a polymer comprising repeating units derived from an ethylenically unsaturated polymerizable monomer (a) having a functional group for fixing a biologically active substance, wherein the polymer has a reactive functional group on at least one terminal side thereof, and a biochip substrate wherein a layer containing the polymer compound is formed on a substrate surface, thereby attaining the object.

24 Claims, No Drawings

(56) References Cited

FOREIGN PATENT DOCUMENTS

| | | |
|---|---|---|
| JP | 2002-293824 | 10/2002 |
| JP | 2003-077129 | 6/2003 |
| JP | 2003-301059 | 10/2003 |
| JP | 2004-279204 | 11/2004 |
| JP | 2004-361387 | 12/2004 |
| JP | 2005-8863 | 1/2005 |
| JP | 2005-10004 | 1/2005 |
| JP | 2006-17458 | 1/2006 |
| JP | 2006-176720 | 7/2006 |
| JP | 2006-184015 | 7/2006 |
| JP | 2006-184016 | 7/2006 |
| WO | WO 03/000433 | 1/2003 |
| WO | WO 03/046562 A1 * | 5/2003 ............ G01N 33/53 |
| WO | 2005/029095 A1 | 3/2005 |

\* cited by examiner

POLYMER COMPOUND FOR MEDICAL MATERIAL, AND BIOCHIP SUBSTRATE USING THE POLYMER COMPOUND

TECHNICAL FIELD

The present invention relates to a polymer compound for medical material having a function of fixing a biologically active substance, a surface coating material containing the polymer compound, and a biochip substrate using the polymer compound.

BACKGROUND ART

Conventionally, various attempts to evaluate genetic activity or decode biological processes, such as a disease process or a biological process of pharmacological effect, have been focused on genomics. However, proteomics can provide more detailed information about the biological function of cells. Proteomics includes qualitative and quantitative measurement of gene activity by detecting and quantifying expressions at the level of proteins rather than the level of genes. Proteomics also includes studies of events which are not coded to genes, such as a post-translational modification of protein and an interaction between proteins.

At present, an enormous volume of genome information has been able to be gained. Accordingly, for researches on proteomics, rapidness and high efficiency (high throughput) have been increasingly demanded. DNA chips have been come into practical use as molecular arrays for this purpose. On the other hand, in order to detect proteins which are the most complicated and the most variable in biological functions, there are proposed protein chips, which are enthusiastically studied in these days. A protein chip is a collective term used to refer to any device in which a protein or a molecule for catching a protein is fixed on a surface of a chip (a fine substrate or particle).

At present, protein chips are generally developed as an extension of DNA chips. Therefore, attempts are made for fixing a protein or a molecule for catching such a protein, into a spot form, onto a surface of a chip such as a glass substrate (see, e.g., Patent Document 1). For example, the fixation of a protein by physical absorption thereof, and others are performed. In such a protein chip, it is preferred that high signals are outputted therefrom; thus, a chip having a high capability of fixing a protein or a molecule for catching it onto a surface of a chip is being desired.

In the meantime, in the detection of signals from a protein chip, a cause of lowering the signal to noise ratio is nonspecific adsorption of a target substance to be detected onto a substrate (see, e.g., Non-Patent Document 1).

In the above-mentioned fixation of a protein by physical adsorption thereof, adsorption preventing agents are coated in order to prevent nonspecific adsorption of a secondary antibody after the protein is fixed. However, the ability of these agents for preventing the nonspecific adsorption is not sufficient. Moreover, the biochip is coated with the adsorption preventing agent after a primary antibody is fixed; therefore, there is caused a problem that the fixed protein is coated so that the reactivity with the secondary antibody deteriorates. For this reason, there is a need for a biochip capable of decreasing the nonspecific adsorption amount of a biologically active substance without being coated with any adsorption preventing agent after a primary antibody is fixed.

In order to decrease the nonspecific adsorption amount of a biologically active substance onto a biochip, it is effective to improve the hydrophilicity of the biochip. However, in the case that such a biochip is used, since the chip has a high hydrophilicity, there is a problem that the protein or the molecule for catching the protein which is fixed on the substrate flows out in the washing process after the protein is caught, so that the signals therefrom decrease. As one approach to this problem, there is disclosed a method of coating a supporting substrate with an active component containing a functional group, a spacer group and a bonding group, a cross-linking component and a matrix-forming component and then curing them, whereby a functional surface strongly bonded with the upper of the supporting substrate can be formed (e.g. Patent Document 2). However, in this disclosed method, although the curing of low molecular components advances on the supporting substrate, the curing reaction involves a shrinkage in the volume of the reactants, so that the supporting substrate may be warped or deformed if the supporting substrate is a plastic substrate. Moreover, a matrix in the form of a network is formed, so as to cause problems that the reaction of the functional group for fixing a biologically active substance may be adversely restricted, and that the reproducibility of the functional expression of the fixed biologically active substance is poor. Furthermore, even if the chip is washed, the protein infiltrated into the inside of the matrix is not completely removed. Thus, there also remains a problem that the nonspecific adsorption cannot be inhibited sufficiently.

Patent Document 1: Japanese Patent Application Laid-Open No. 2001-116750.
Patent Document 2: Japanese Patent Application National Publication (Laid-Open) No. 2004-531390.
Non-Patent Document 1: Hayashizaki, Y. and Okazaki, K., 2000, "Practical Manual of DNA Microarray". P. 57, Yodosha Co., Ltd., Tokyo.

DISCLOSURE OF THE INVENTION

Problem to be Solved by the Invention

An object of the present invention is to provide a polymer compound for medicine which has an excellent capability of fixing a biologically active substance and has such chemical/physical stability that the compound is less dissolved or deteriorated in a washing step, in particular, which can be suitably applied to a plastic substrate surface; provide a polymer compound for medicine which less exhibits nonspecific adsorption to proteins as well as which has the above-mentioned characteristics; and provide a biochip substrate showing a high SN ratio using the polymer compound.

Means for Solving the Problems

The inventors have studied enthusiastically in order to develop a polymer compound for medical material which is excellent in capability of fixing a biologically active substance and less exhibits nonspecific adsorption to proteins. As a result, the inventors have found out that: a polymer compound for medical material which is a copolymer made from an ethylenically unsaturated polymerizable monomer (a) having a functional group for fixing a biologically active substance and which has, on at least one terminal side thereof, a reactive functional group is excellent in capability of fixing the biologically active substance, has such chemical/physical stability that the compound is less dissolved or deteriorated in a washing step, and can be uniformly applied onto a plastic substrate also without causing a warp, undulations or other problems; and the nonspecific adsorption of proteins and others thereto can be further decreased by adding a component made of an ethylenically unsaturated polymerizable monomer (b) having an alkylene glycol residue to the component of the polymer compound. Furthermore, the inventors have found out that these polymer compounds for medical material are preferably used for biochips. Thus, the present invention has been made.

Accordingly, the present invention is:

(1) a polymer compound for medical material which is a polymer comprising repeating units derived from an ethylenically unsaturated polymerizable monomer (a) having a functional group for fixing a biologically active substance, wherein the polymer has a reactive functional group on at least one terminal side thereof;

(2) a polymer compound for medical material which is a copolymer comprising repeating units derived from an ethylenically unsaturated polymerizable monomer (a) having a functional group for fixing a biologically active substance, and an ethylenically unsaturated polymerizable monomer (b) having an alkylene glycol residue, wherein the copolymer has a reactive functional group on at least one terminal side thereof;

(3) a polymer compound for medical material which is a copolymer comprising repeating units derived from an ethylenically unsaturated polymerizable monomer (a) having a functional group for fixing a biologically active substance, an ethylenically unsaturated polymerizable monomer (b) having an alkylene glycol residue, and an ethylenically unsaturated polymerizable monomer (c) having a hydrophobic unit, wherein the copolymer has a reactive functional group on at least one terminal side thereof;

(4) the polymer compound for medical material according to any one of (1) 1 to (3), wherein the reactive functional group on the terminal is a reactive silyl group;

(5) the polymer compound for medical material according to (4), wherein the reactive silyl group is an alkoxysilyl group;

(6) The polymer compound for medical material according to any one of (1) to (5), wherein the functional group of the ethylenically unsaturated polymerizable monomer (a) having a functional group for fixing a biologically active substance is at least one functional group selected from an aldehyde group, an active ester group, an epoxy group, a vinylsulfone group, and biotin;

(7) the polymer compound for medical material according to any one of (1) to (6), wherein the ethylenically unsaturated polymerizable monomer (a) having a functional group for fixing a biologically active substance is a monomer having an active ester group and represented by the following general formula [1]:

[Formula 1]

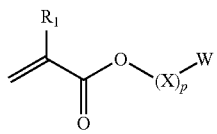

[1]

wherein $R_1$, represents a hydrogen atom or a methyl group, X represents an alkyl group or an alkylene glycol residue having 1 to 10 carbon atoms, W represents an active ester group, and p represents an integer from 1 to 100 provided that when p is an integer of 2 or more and 100 or less, the repeated Xs may be the same or different;

(8) the polymer compound for medical material according to claim 6 or 7, wherein the active ester group is a p-nitrophenyl ester or N-hydroxysuccinimide ester;

(9) the polymer compound for medical material according to any one of (2) to (8), wherein the ethylenically unsaturated polymerizable monomer (b) having an alkylene glycol residue is a monomer represented by the following general formula [2]:

[Formula 2]

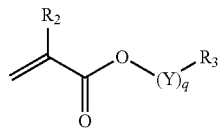

[2]

wherein $R_2$ represents a hydrogen atom or a methyl group, $R_3$ represents a hydrogen atom or an alkyl group having 1 to 20 carbon atoms, Y represents an alkylene glycol residue having 1 to 10 carbon atoms, and q represents an integer from 1 to 100 provided that when q is an integer of 2 or more and 100 or less, the repeated Ys may be the same or different;

(10) the polymer compound for medical material according to any one of (2) to (9), wherein the ethylenically unsaturated polymerizable monomer (b) having an alkylene glycol residue is methoxypolyethylene glycol(meth)acrylate or ethoxypolyethylene glycol(meth)acrylate;

(11) the polymer compound for medical material according to (10), wherein the average repeating number of the ethylene glycol residues in the methoxypolyethylene glycol (meth)acrylate or ethoxypolyethylene glycol(meth)acrylate is from 3 to 100;

(12) the polymer compound for medical material according to any one of (3) to (11), wherein the hydrophobic group of the ethylenically unsaturated polymerizable monomer (c) having a hydrophobic group is an alkyl group;

(13) the polymer compound for medical material according to any one of (3) to (12), wherein the hydrophobic group of the ethylenically unsaturated polymerizable monomer (c) having a hydrophobic group is an alkyl group having 3 to 20 carbon atoms;

(14) the polymer compound for medical material according to (13), wherein the ethylenically unsaturated polymerizable monomer (c) having a hydrophobic group is at least one monomer selected from n-butyl methacrylate, n-dodecyl methacrylate, n-octyl methacrylate, and cyclohexyl methacrylate;

(15) a process for producing a polymer compound for medical material defined by any one of (1) to (14), wherein at least an ethylenically unsaturated polymerizable monomer (a) having a functional group for fixing a biologically active substance is subjected to radical polymerization in the presence of a mercapto compound (d) having a reactive functional group to obtain the polymer compound having the reactive functional group introduced to the terminal thereof;

(16) a process for producing a polymer compound for medical material defined by any one of (2) to (14), wherein at least an ethylenically unsaturated polymerizable monomer (a) having a functional group for fixing a biologically active substance and an ethylenically unsaturated polymerizable monomer (b) having an alkylene glycol residue are subjected to radical copolymerization in the presence of a mercapto compound (d) having a reactive functional group to obtain the polymer compound having the reactive functional group introduced to the terminal thereof;

(17) the process for producing a polymer compound for medical material according to (15) or (16), wherein the mercapto compound (d) having a reactive functional group is a mercaptosilane compound represented by the following general formula [3]:

[Formula 3]

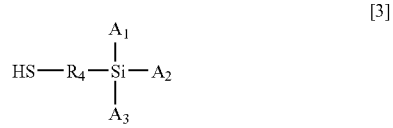

wherein $R_4$ represents an alkyl group having 1 to 20 carbon atoms, and at least one of $A_1$, $A_2$ and $A_3$ is a reactive moiety, and the others are each an alkyl group;

(18) the process for producing a polymer compound for medical material according to (17), wherein the reactive moiety of the mercaptosilane compound represented by the general formula [3] is an alkoxyl group;

(19) a surface coating material for medical material, which comprises a polymer compound for medical material according to anyone of (1) to (14), or a polymer compound for medical material obtained by the producing process according to any one of (15) to (18);

(20) a biochip substrate, wherein a layer comprising a surface coating material for medical material according to (19) is formed on a surface of a substrate;

(21) the biochip substrate according to (20), wherein the substrate is made of a plastic;

(22) the biochip substrate according to (21), wherein the plastic is a saturated cyclic polyolefin;

(23) a biochip, wherein a biologically active substance is fixed to a biochip substrate according to any one of (20) to (22); and

(24) the biochip according to (23), wherein the biologically active substance is at least one biologically active substance selected from nucleic acid, aptamer, protein, oligopeptide, sugar chain and glycoprotein.

Effect of Invention

According to the present invention, it is possible to provide a polymer compound which has an excellent capability of fixing a biologically active substance and has such chemical/physical stability that the compound is less dissolved or deteriorated in a washing step, in particular, which can be suitably applied to a plastic substrate surface. By adding, to the polymer compound component, an ethylenically unsaturated polymerizable monomer (b) having an alkylene glycol residue, it is possible to provide a polymer compound for medicine to which proteins are less subjected to nonspecific adsorption. Furthermore, it is possible to provide a biochip substrate exhibiting a high SN ratio, using this polymer compound.

BEST MODE FOR CARRYING OUT THE INVENTION

The polymer compound of the present invention is a polymer compound for medical material which is a polymer comprising repeating units derived from an ethylenically unsaturated polymerizable monomer (a) having a functional group for fixing a biologically active substance, the polymer has a reactive functional group on at least one terminal side thereof. This polymer compound has a nature of fixing a specific biologically active substance. Furthermore, the compound has, on at least one terminal side thereof, a reactive functional group; thus, the compound becomes able to form a covalent bond to a substrate, thereby making it possible to cause the polymer compound to be grafted onto a surface of the substrate. About the thus-obtained grafted substrate, the polymer compound does not flow out therefrom in a washing step. Moreover, the polymer compound does not need a curing reaction involving a shrinkage in the volume, and a highly-grown network structure is not basically formed in the film of the polymer compound formed on the substrate. Therefore, the polymer compound can be uniformly applied onto a plastic substrate also without causing a warp, undulations or other problems.

Furthermore, when thereto are added repeating units derived from an ethylenically unsaturated polymerizable monomer (b) having an alkylene glycol residue, as a component of the polymer compound, the alkylene glycol residue performs a function of inhibiting the nonspecific adsorption of proteins. Accordingly, the nature of inhibiting the nonspecific adsorption of a biologically active substance is promoted.

In the ethylenically unsaturated polymerizable monomer (a) having a functional group for fixing a biologically active substance to be used in the invention, the functional group may be a chemically active group, receptor group or ligand group, but is not limited thereto. Specific examples thereof include an aldehyde group, an active ester group, an epoxy group, a vinylsuflone group, biotin, a thiol group, an amino group, an isocyanate group, an isothiocyanate group, a hydroxyl group, an acrylate group, a maleimide-group, a hydrazide group, an azide group, an amide group, a sulfonate group, streptavidin, and metal chelates, but the functional group is not limited thereto. Among them, preferred are an aldehyde group, an active ester group, an epoxy group, and a vinylsulfone group from the viewpoint of the reactivity thereof with an amino group, which is contained in an biologically active substance in many cases. Moreover, biotin is preferred since it has a high binding constant onto a biologically active substance. In particular, an active ester group is most preferred from the viewpoint of the storage stability of the monomer.

The ethylenically unsaturated polymerizable monomer (a) having a functional group for fixing a biologically active substance to be used in the invention is not particularly limited about the structure thereof. The monomer (a) is preferably a compound represented by a general formula [1] illustrated below, wherein a (meth)acrylic group and an active ester group are bonded to each other through a chain of an alkyl group or an alkylene glycol residue which has 1 to 10 carbon atoms. In particular, a chain of an alkylene glycol residue itself has a nature of inhibiting the nonspecific adsorption of proteins. For this reason, a monomer wherein a (meth)acrylic group and an active ester group are bonded to each other through a chain of an alkylene glycol residue has both of a nature of fixing a biologically active substance and a nature of inhibiting the nonspecific adsorption of proteins. Accordingly, even if a polymer from such a monomer is a homopolymer, the polymer can be preferably used as a polymer compound for medical material as long as the polymer has, on at least one terminal side thereof, a reactive functional group. In the invention, (meth)acrylic means acrylic and/or methacrylic, and (meth)acrylate means acrylate and/or methacrylate.

[Formula 4]

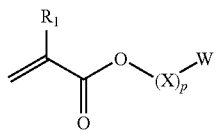

wherein $R_1$ represents a hydrogen atom or a methyl group, X represents an alkyl group or an alkylene glycol residue having 1 to 10 carbon atoms, W represents an active ester group, and p represents an integer from 1 to 100 provided that when p is an integer of 2 or more and 100 or less, the repeated Xs may be the same or different.

When X is an alkylene glycol residue in the formula [1], X has 1 to 10 carbon atoms, preferably 1 to 6 carbon atoms, more preferably 2 to 4 carbon atoms, even more preferably 2 to 3 carbon atoms, most preferably 2 carbon atoms. The alkylene glycol residue referred to herein means an alkyleneoxy group (—R—O, wherein R is an alkylene group) which remains after a hydroxyl group at a single terminal or hydroxyl groups at both terminals of an alkylene glycol (HO—R—OH wherein R is the alkylene group) are subjected to condensation reaction with a different compound. For example, in the case of methylene glycol (OH—$CH_2$—OH), the alkylene glycol residue is a methyleneoxy group (—$CH_2$—O—); and in the case of ethylene glycol (OH—$CH_2CH_2$—OH), the alkylene glycol residue is an ethyleneoxy group (—$CH_2CH_2$—O—)

The repeating number p of Xs is an integer from 1 to 100. When X is an alkylene glycol residue, the number p is more preferably an integer from 2 to 50, even more preferably an integer from 2 to 30, most preferably an integer from 2 to 20. In the case of a mixture of polymer compound species the numbers p's of which are various, the number p of the entire species of the polymer compound is specified as the average value of the above. When the repeating number p is 2 or more, the repeated Xs may be the same or different.

When Xs are each an alkyl group in the formula [1], the total number $((X)_p)$ of the carbon atoms in the alkyl groups the number of which is p is preferably from 1 to 100, more preferably from 1 to 20. The alkyl group is not particularly limited about the structure thereof, and may be linear, branched or cyclic.

The "active ester group" used in the invention means an ester group activated relative to a nucleophilic reaction by having a high acidic electron attracting group as one substituent of the ester group, that is an ester group having a high reaction activity, which is conventionally used in various chemical synthesis such as in a field of polymer chemistry, or in a field of peptide synthesis. Actually, phenol esters, thiophenol esters, N-hydroxyamine esters, esters of a heterocyclic hydroxy compound and so on are each known as an active ester group having a much higher activity than that of alkyl esters or the like.

Such an active ester group may be an ester wherein R" in —COOR" has the above-mentioned high acidic electron attracting group. Examples thereof include a p-nitrophenyl active ester group, wherein R" is p-nitrophenyl; an N-hydroxysuccinimide active ester group, wherein R" is N-hydroxysuccinimide; a phthalic imide active ester group, wherein R" is phthalic imide; and a 5-norbornene-2,3-dicarboxylmide active ester group, wherein R" is 5-norbornene-2,3-dicarboxylmide. In particular, a p-nitrophenyl active ester group or N-hydroxysuccinimide active ester group is preferred from the viewpoint of height in storage stability and reactivity, and balance therebetween. A p-nitrophenyl active ester group is most preferred.

Examples of the ethylenically unsaturated polymerizable monomer (a) having a functional group for fixing a biologically active substance include p-nitrophenyloxycarbonyl-poly(ethylene glycol)(meth)acrylate, and succinimideoxycarbonylpoly(ethylene glycol)(meth)acrylate. In particular, p-nitrophenyloxycarbonyl-poly(ethylene glycol)(meth)acrylate represented by a formula illustrated below is preferred. The repeating number p of the ethylene glycols and/or the average value of p is preferably from 2 to 20.

[Formula 5]

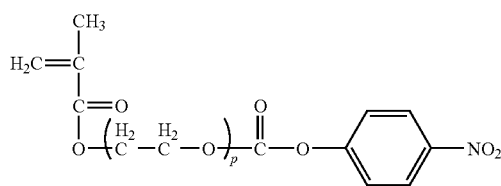

In the polymer compound of the invention, the ratio of portions derived from the ethylenically unsaturated polymerizable monomer (a) having a functional group for fixing a biologically active substance is not particularly limited, and is preferably from 1 to 99.7% by mol of the total number of repeating units of all monomers in the polymer, more preferably form 1 to 70% by mol thereof, most preferably from 1 to 50% by mol thereof.

The ethylenically unsaturated polymerizable monomer (b) having an alkylene glycol residue to be used in the invention is not particularly limited about the structure thereof, and is preferably a compound represented by a general formula [2] illustrated below, which is composed of a (meth)acrylic group and a chain of an alkylene glycol residue Y having 1 to 10 carbon atoms.

[Formula 6]

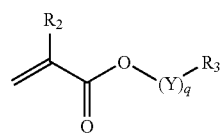

wherein $R_2$ represents a hydrogen atom or a methyl group, $R_3$ represents a hydrogen atom or an alkyl group having 1 to 20 carbon atoms, Y represents an alkylene glycol residue having 1 to 10 carbon atoms, and q represents an integer from 1 to 100 provided that when q is an integer of 2 or more and 100 or less, the repeated Ys may be the same or different.

The alkylene glycol residue Y in the formula has 1 to 10 carbon atoms, preferably 1 to 6 carbon atoms, more preferably 2 to 4 carbon atoms, even more preferably 2 to 3 carbon atoms, most preferably 2 carbon atoms. The repeating number q of the alkylene glycol residues Ys is not particularly limited, and is preferably an integer from 1 to 100, more preferably from an integer from 2 to 100, even more preferably an integer from 2 to 95, most preferably an integer from 20 to 90. In the case of a mixture of polymer compound species the numbers q's of which are various, the number q of the entire species of the polymer compound is specified as the average value of the above. When the repeating number q is 2 or more, Ys may be the same or different.

Examples of the ethylenically unsaturated polymerizable monomer (b) having an alkylene glycol residue include methoxy polyethylene glycol(meth)acrylate, ethoxy polyethylene glycol(meth)acrylate, 2-hydroxyethyl(meth)acrylate and an ester wherein the hydroxyl group thereof is mono-substituted, 2-hydroxypropyl(meth)acrylate and an ester wherein the hydroxyl group thereof is mono-substituted, 2-hydroxybutyl(meth)acrylate and an ester wherein the hydroxyl group thereof is mono-substituted, glycerol mono(meth)acrylate, (meth)acrylate having polypropylene glycol as its side chain, 2-methoxyethyl(meth)acrylate, 2-ethoxyethyl(meth)acrylate, methoxydiethylene glycol(meth)acrylate, ethoxydiethylene glycol(meth)acrylate, and ethoxypolyethylene glycol (meth)acrylate. Preferred is methoxypolyethylene glycol (meth)acrylate or ethoxypolyethylene glycol(meth)acrylate since the nonspecific adsorption of a biologically active substance is less caused and the (meth)acrylate is easily available. In particular, methoxypolyethylene glycol(meth)acrylate or ethoxypolyethylene glycol(meth)acrylate wherein the average repeating number of ethylene glycol residues is from 3 to 100 is preferably used since the (meth)acrylate is good in handleability when synthesized.

In the polymer compound of the invention, the ratio of portions derived from the ethylenically unsaturated polymerizable monomer (b) having an alkylene glycol residue is not particularly limited, and is preferably from 0 to 95% by mol of the total number of repeating units of all monomers in the polymer, more preferably from 30 to 95% by mol thereof, most preferably from 50 to 90% by mol thereof.

The polymer compound used in the invention may contain another ethylenically unsaturated polymerizable monomer other than the ethylenically unsaturated polymerizable monomer (a) having a functional group for fixing a biologically active substance and the ethylenically unsaturated polymerizable monomer (b) having an alkylene glycol residue as long as the polymer compound has, on at least one terminal side thereof, a reactive functional group. The polymer compound may be a polymer compound obtained by copolymerizing an ethylenically unsaturated polymerizable monomer (c) having a hydrophobic group further therewith since the polymer compound has an improved coatability onto, for example, a plastic substrate. The ethylenically unsaturated polymerizable monomer (c) having a hydrophobic group is not particularly limited about the structure thereof as long as the monomer has a hydrophobic group without having any functional group of fixing a biologically active substance nor any alkylene glycol residue. The hydrophobic group may be a linear, branched or cyclic aliphatic hydrocarbon group, an aromatic hydrocarbon group, or the like. The ethylenically unsaturated polymerizable monomer (c) having a hydrophobic group is preferably a monomer wherein a hydrophobic group is bonded to a (meth)acrylic group ($CH_2=CR_5-COO-$ wherein $R_5$ represents a hydrogen atom or a methyl group). The monomer may be a (meth)acrylate to which an aliphatic hydrocarbon is bonded, or a (meth)acrylate to which an aromatic hydrocarbon is bonded. The monomer is more preferably a (meth)acrylate wherein the hydrophobic group is an alkyl group because of handleability in the synthesis thereof. The monomer is even more preferably a (meth)acrylate wherein the alkyl group is an alkyl group having 3 to 20 carbon atoms. The alkyl group is not particularly limited about the structure thereof, and may be linear, branched or cyclic.

Specific examples of the monomer include n-butyl (meth) acrylate, iso-butyl (meth)acrylate, sec-butyl (meth)acrylate, t-butyl (meth)acrylate, n-neopentyl(meth)acrylate, iso-neopentyl(meth)acrylate, sec-neopentyl(meth)acrylate, neopentyl(meth)acrylate, n-hexyl(meth)acrylate, iso-hexyl(meth) acrylate, heptyl(meth)acrylate, n-octyl(meth)acrylate, iso-octyl(meth)acrylate, 2-ethylhexyl(meth)acrylate, n-nonyl (meth)acrylate, iso-nonyl(meth)acrylate, n-decyl(meth) acrylate, iso-decyl(meth)acrylate, n-dodecyl(meth)acrylate, iso-dodecyl(meth)acrylate, n-tridecyl(meth)acrylate, iso-tridecyl(meth)acrylate, n-tetradecyl(meth)acrylate, iso-tetradecyl(meth)acrylate, n-pentadecyl(meth)acrylate, iso-pentadecyl(meth)acrylate, n-hexadecyl(meth)acrylate, iso-hexadecyl(meth)acrylate, n-octadecyl(meth)acrylate, iso-octadecyl(meth)acrylate, cyclohexyl(meth)acrylate, and isobornyl(meth)acrylate. Among them, most preferred are n-butyl methacrylate, n-dodecyl methacrylate, n-octyl methacrylate, and cyclohexyl methacrylate since they are easily available.

In the polymer compound of the invention, the ratio of portions derived from the ethylenically unsaturated polymerizable monomer (c) having a hydrophobic group is not particularly limited, and is preferably from 0 to 90% by mol of the total number of repeating units of all monomers in the polymer, more preferably from 0 to 80% by mol thereof, most preferably from 0 to 70% by mol thereof. If the composition ratio of the ethylenically unsaturated polymerizable monomer (c) in the polymer is more than the upper limit, it is feared that the nonspecific adsorption of a biologically active substance such as a protein increases.

The reactive functional group introduced into at least one terminal side of the polymer is not particularly limited as long as the group is a functional group which can be covalently bonded to a surface of such a substrate as used in a biochip substrate. In accordance with a functional group present on the surface of the used substrate, a reactive functional group which can be covalently bonded thereto can be appropriately selected. As will be described later, since the used substrate is usually a plastic, glass substrate, or the like in many cases, a hydroxyl group, an amino group, an aldehyde group, a carboxyl group, or the like can be introduced to the surface thereof. Thus, the reactive functional group introduced to the terminal can be, for example, a reactive silyl group, an epoxy group, or an amino group.

In particular, the reactive functional group introduced into at least one terminal side of the polymer is preferably a reactive silyl group since the group can be caused to react with the substrate under a relatively mild condition. The reactive silyl group is a functional group which generates a silanol group by hydrolysis, a silanol group, or the like. The functional group which generates a silanol group by hydrolysis is a group which is easily hydrolyzed when it contacts water, so that a silanol group is generated. The reactive silyl group may be a structure represented by the following general formula [4]:

[Formula 7]

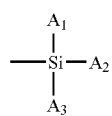

[4]

wherein at least one of $A_1$, $A_2$ and $A_3$ is a reactive moiety in the reactive functional group, and the others are each an alkyl group. The reactive moiety is a moiety which can be covalently bonded to a substrate. Examples of the reactive moiety include an alkoxyl group, a halogen group, an amino group, a isocyanate group, a phenoxy group, and a hydroxyl group.

Preferred examples of the reactive functional group include a halogenated silyl group (≡—Si—X wherein X is a halogen group), an alkoxysilyl group (≡—Si—OR wherein R is an alkyl group), a phenoxysilyl group (≡Si—OPh wherein Ph is a phenyl group), and an acetoxysilyl group (≡Si—OOCCH₃). An alkoxysilyl group, a phenoxysilyl group, and an acetoxysilyl group are preferred since they contain no halogen. Among them, an alkoxysilyl group is in particular preferred since the group easily generates a silanol group.

The introduction ratio of the reactive functional group introduced into at least one terminal side of the polymer is preferably from 0.2 to 10% by mol of the total number of the repeating units of all monomers in the polymer, more preferably from 0.5 to 5% by mol thereof.

The method for introducing the reactive functional group into the terminal is not particularly limited, and is preferably a method of subjecting at least the ethylenically unsaturated polymerizable monomer (a) having a functional group for fixing a biologically active substance to radical polymerization in the presence of a mercapto compound (d) having a reactive functional group in a solvent since this method is simple and easy. If necessary, the monomer (b), the monomer (c) and others may be added thereto. Since the mercapto compound (d) having a reactive functional group acts as a chain transfer agent, a polymer compound having a reactive functional group at its terminal is obtained. The mercapto compound (d) having a reactive functional group is not particularly limited, and is preferably a mercaptosilane compound represented by the following general formula [3]:

[Formula 8]

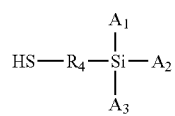

[3]

wherein $R_4$, which is an alkyl group, has 1 to 20 carbon atoms, more preferably 1 to 5 carbon atoms, most preferably 1 to 3 carbon atoms, at least one of $A_1$, $A_2$ and $A_3$ is a reactive moiety of a reactive functional group, and the others are each an alkyl group. Examples of the reactive moiety include an alkoxy group, a halogen group, an amino group, a isocyanate group, a phenoxy group, and a hydroxyl group. In particular, an alkoxy group is most preferred since the group easily generates a silanol group. When the polymer is required to be stored for a long term, it is preferred that only one reactive moiety is present in the reactive functional group since the polymer gives a good storability.

Examples of the mercaptosilane compound having an alkoxyl group include (3-mercaptopropyl)trimethoxysilane, (3-mercaptopropyl)methyldimethoxysilane, (3-mercaptopropyl)dimethylmethoxysilane, (3-mercaptopropyl)triethoxysilane, (3-mercaptopropyl)methyldiethoxysilane, (3-mercaptopropyl)dimethylethoxysilane, (mercaptomethyl)trimethoxysilane, (mercaptomethyl)methyldimethoxysilane, (mercaptomethyl)dimethylmethoxysilane, (mercaptomethyl)triethoxysilane, (mercaptomethyl)methyldiethoxysilane, and (mercaptomethyl)dimethylethoxysilane, but the mercaptosilane compound is not limited thereto. From the viewpoint of availability, (3-mercaptopropyl)trimethoxysilane and (3-mercaptopropyl)triethoxysilane are preferred. In particular, when the polymer is required to be stored for a long term, (3-mercaptopropyl)dimethylethoxysilane is more preferred since the polymer gives a good storability. These mercaptosilane compounds are used alone or in combination of two or more thereof.

The solvent is not limited to any special solvent insofar as each of ethylenically unsaturated polymerizable monomers and the mercapto compound (d) having a reactive functional group can be dissolved therein. Examples thereof include methanol, ethanol, t-butyl alcohol, benzene, toluene, tetrahydrofuran, dioxane, dichloromethane, and chloroform. These solvents are used alone or in combination of two or more thereof. When the present polymer compound is applied onto a plastic substrate, ethanol and methanol are preferred in view of avoiding the denaturation of the substrate.

The polymerization initiator may be any ordinary radical initiator. Examples thereof include azo compounds such as 2,2'-azobisisobutylnitrile (hereinafter referred to as "AIBN") and 1,1'-azobis(cyclohexane-1-carbonitrile), and organic peroxides such as benzoyl peroxide, and lauryl peroxide.

About the chemical structure of the polymer compound of the invention, the bonding manner thereof in the case that the polymer is a copolymer may be any manner, such as a random, block or graft manner, as long as the copolymer is a copolymer which contains repeating units derived from at least the individual ethylenically unsaturated polymerizable monomers having a functional group for fixing a biologically active substance and which has a reactive functional group on at least one terminal thereof.

About the molecular weight of the polymer compound of the invention, the number-average molecular weight is preferably 5,000 or more and 1,000,000 or less, more preferably 10,000 or more and 500,000 or less since the polymer compound is uniformly applied onto a substrate with ease and further the polymer compound is easily separated and purified from the ethylenically unsaturated polymerizable monomer(s) unreacted. The number-average molecular weight referred to herein is a number-average molecular weight calculated from the composition obtained by analysis of NMR measurement on the supposition that a reactive functional group is introduced into a single terminal of each of the polymer molecules.

In the case of using a mixture of the ethylenically unsaturated polymerizable monomer (a) having a functional group for fixing a biologically active substance, the ethylenically unsaturated polymerizable monomer (b) having an alkylene glycol residue, the ethylenically unsaturated polymerizable monomer (c) having a hydrophobic group and so on without copolymerizing each of monomer components in advance, applying the components onto a substrate, and causing curing reaction of the components after the applying, the mixture of the monomer components may not be uniformly applied on the substrate because of the compatibility thereof with the substrate or compatibility between the monomer components. On the other hand, when the monomer components are beforehand copolymerized as in the invention, so as to prepare a polymer compound, the polymer compound can be uniformly applied onto a substrate.

The polymer compound of the invention is different from a resin wherein a network matrix is formed by crosslinking, and is characterized in that the compound is easily dissolved in an organic solvent which will be described later, such as ethanol, even after the compound is applied into a thickness of about 0.1 to 1 μm onto a substrate (a substrate having an inactive surface which is not covalently bonded to the reactive functional group that the polymer compound has) and then the resultant is subjected to heating treatment. As the above-mentioned substrate, there may be used a polyolefin resin substrate and the like in which the substrate is not subjected to a surface treatment for activating the substrate surface, which will be described later. As the heating treatment, for example, there may be a heating treatment at 60 to 120° C. for 5 minutes to 24 hours.

By coating a substrate surface with the polymer compound of the invention, the polymer compound can easily give a nature of fixing a specific biologically active substance thereto. When an alkylene glycol residue is present in the components of the polymer compound, the polymer compound gives a nature of inhibiting the nonspecific adsorption of proteins as well as the nature of fixing a specific biologically active substance. Furthermore, the reactive group at the terminal can be bonded to the substrate, so that the polymer compound can be chemically grafted. For this reason, it is not feared that a deterioration of signals is caused by washing the substrate.

The coating of the polymer compound onto the substrate surface may be, for example, by preparing a polymer solution wherein the polymer compound is dissolved in an organic solvent to have a concentration of 0.05 to 10% by weight, applying the solution onto the substrate surface by a known process such as dipping or blowing, and then drying the resultant at room temperature or at a raised temperature. The organic solvent may be ethanol, methanol, t-butyl alcohol, benzene, toluene, tetrahydrofuran, dioxane, dichloromethane, chloroform, acetone, methyl ethyl ketone, or some other single solvent; or a mixed solvent thereof. In particular, ethanol and methanol are preferred since the alcohols do not cause denaturation of the plastic substrate, and the alcohols are easily dried.

The polymer compound of the invention can be covalently bonded to a substrate by use of its terminal reactive functional group. Conditions for the bonding may be selected arbitrarily in accordance with the functional group. In the case that the polymer compound is, for example, a polymer compound having an alkoxysilyl group at its terminal, a silanol group generated by the hydrolysis undergoes dehydration condensation with a hydroxyl group, an amino group, a carbonyl group, a silanol group or the like on the substrate surface, so as to form covalent bonds. The covalent bonds formed by the dehydration condensation of the silanol group have a nature that the bonds are not easily hydrolyzed. Thus, the polymer compound grafted on the substrate surface is not easily dissolved or separated from the substrate. The dehydration condensation of the silanol group is promoted by heating treatment. The heating treatment is preferably in the range of temperatures at which the polymer compound is not denatured by heat, for example, in the range of 60 to 120° C. for 5 minutes to 24 hours.

In the case that an organic solvent having a high polarity such as ethanol or methanol is used or the hydrophilicity of the polymer compound itself is high, the alkoxysilyl group at the polymer terminal is hydrolyzed by water contained in the solvent or water in the air after the solution is applied. In many cases, therefore, the polymer compound can be grafted only by heating the substrate even if the polymer does not undergo any special hydrolysis step. When the hydrolysis is insufficient, it is allowable to use a mixed solution wherein water is incorporated into an organic solvent. Theoretically, a sufficient result is produced when water necessary for generating a silanol group is supplied; however, the water content is preferably 15% or less by weight, considering easiness of the preparation of the solution. If the water content is large, it is feared that the polymer compound is not dissolved in the solvent.

The material of the biochip substrate used in the invention may be a glass, a plastic, a metal or the like. A plastic is preferred, and in particular a thermoplastic resin is more preferred from the viewpoint of easiness of the surface treatment thereof, and the mass productivity.

The thermoplastic resin is preferably a thermoplastic from which fluorescence is less generated. The resin is preferably, for example, a linear polyolefin such as polyethylene or polypropylene, a cyclic polyolefin, or a fluorine-contained resin, and is more preferably a saturated cyclic polyolefin particularly good in heat resistance, chemical resistance, low fluorescence and moldability. In this context, the saturated cyclic polyolefin means a saturated polymer obtained by hydrogenating a homopolymer having a cyclic olefin structure, or a copolymer made from a cyclic olefin and an α-olefin.

In order to graft the polymer compound onto a substrate, it is preferable to activate the surface of the substrate. An activating method may be a method of conducting a plasma treatment under a condition such as oxygen atmosphere, argon atmosphere, nitrogen atmosphere, or air atmosphere, or may be a method of conducting a treatment with excimer laser such as ArF or KrF. Particularly, the method of conducting a plasma treatment in oxygen atmosphere is preferable.

By applying the polymer compound of the invention onto the substrate, it is possible to produce easily a biochip substrate wherein the capability of fixing a biologically active substance is excellent and the nonspecific adsorption of the biologically active substance onto the substrate is inhibited. Moreover, the polymer compound does not flow out in a washing step since the polymer compound can be bonded to the substrate by chemical bonding. On the basis of these matters, the substrate coated with the polymer compound can be preferably used as a biochip.

By use of the biochip substrate of the invention, various biologically active substances can be fixed thereto. The biologically active substance to be fixed is nucleic acid, aptamer, protein, oligopeptide, sugar chain, glycoprotein or the like. In the case of fixing, for example, nucleic acid, it is preferred to introduce an amino group into nucleic acid in order to make the reactivity with the active ester group high. The position where the amino group is introduced may be a terminal or a side chain of the molecular chain. However, it is preferable that the amino group is introduced at an end of a molecular chain.

When a biologically active substance is fixed onto the biochip substrate in the invention, it is preferred to use a method of spotting a liquid wherein the biologically active substance is dissolved or dispersed.

When the liquid is allowed to stand still after the spotting, the biologically active substance is fixed onto the surface. In the case of using, for example, aminated nucleic acid, the liquid is allowed to stand still in the range of room temperature to 80° C. for 1 hour, thereby attaining the fixation. The higher process temperature is preferable. The liquid in which the biologically active substance is dissolved or dispersed is preferably alkaline.

After the resultant is washed, functional groups on the substrate surface excluding the area where the biologically active substance is fixed are subjected to inactivating treatment. In the case of an active ester or an aldehyde group, the treatment is preferably conducted by use of an alkaline compound or a compound having a primary amine group.

Examples of the alkali compound which can be preferably used include sodium hydroxide, potassium hydroxide, sodium carbonate, sodium hydrogencarbonate, disodium hydrogenphosphate, calcium hydroxide, magnesium hydroxide, sodium borate, lithium hydroxide, potassium phosphate and the like.

Examples of the compound having a primary amino group which can be preferably used include methylamine, ethylamine, butylamine, glycine, 9-aminoaquagene, aminobutanol, 4-aminobutyric acid, aminocapric acid, aminoethanol, 5-amino 2,3-dihydro-1,4-pentanol, aminoethanethiol hydrochloride, aminoethanethiolsulfuric acid, 2-(2-aminoethylamino)ethanol, 2-aminoethyldihydrogenphosphate, aminoethylhydrogensulfate, 4-(2-aminoethyl)morpholine, 5-aminofluorescein, 6-aminohexanoic acid, aminohexylcellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino 2-propanol, 3-amino-1-propanol, 3-aminopropene, 3-aminopropionitrile, aminopyridine, 11-aminoundecanoic acid, aminosalicylic acid, aminoquinoline, 4-aminophtalonitrile, 3-aminophthalimide, p-aminopropiophenone, aminophenylacetic acid, aminonaphthalene and the like. Aminoethanol and glycine are most preferred.

The biochip thus obtained by fixing the biologically active substance as described can be used for various analysis systems including immunodiagnosis, a gene microarray, a protein microarray, and a microfluidic device.

EXAMPLES

Synthesis of p-Nitrophenyloxycarbonyl-Polyethylene Glycol Methacrylate (MEONP)

Into 20 mL of chloroform was dissolved 0.01 mol of polyethylene glycol monomethacrylate (Blenmer PE-200 manufactured by NOF Corp.), and then the solution was cooled to −30° C. While the temperature was maintained at −30° C., into this solution was slowly dropped a homogeneous solution prepared in advance and made of 0.01 mol of p-nitrophenyl chloroformate (available from Aldrich Co.), 0.01 mol of triethylamine (available from Wako Pure Chemical Industries, Ltd.), and 20 mL of chloroform. The reactive components were caused to react at −30° C. for 1 hour, and then the solution was further stirred at room temperature for 2 hours. Thereafter, salts are filtrated off from the reaction solution, and the solvent was removed so that p-nitrophenyloxycarbonyl-polyethylene glycol methacrylate (MEONP) was obtained. The resultant monomer was measured by $^1$H-NMR in a solution of heavy chloroform. As a result, it was confirmed that 4.5 units of ethylene glycol residues were contained.

Synthesis Example 1 of Polymer Compound

Polyethylene glycol methyl ether methacrylate having a number-average molecular weight Mn of about 1100 (also known as methoxypolyethylene glycol methacrylate, which will be referred to as PEGMA1100 hereinafter, and was available from Aldrich Co.), and p-nitrophenyloxycarbonyl-polyethylene glycol methacrylate (hereinafter referred to as MEONP) were dissolved in dehydrated ethanol, so as to prepare a monomer mixed solution. The total concentration of the monomers was 0.3 mol/L. About the mol ratio between the individual monomers, the ratio of PEGMA100 to MEONP was 85 to 15. Furthermore, thereto were added (3-mercaptopropyl)trimethoxysilane (hereinafter referred to as MPTMS and available from Aldrich Co.) and 2,2-azobisisobutyronitrile (hereinafter referred to as AIBN and available from Wako Pure Chemical Industries, Ltd.) so as to set the concentration of each of these components to 0.003 mol/L. The solution was stirred until the solution turned into a homogeneous state. Thereafter, in the atmosphere of argon gas, the reactive components were caused to react at 60° C. for 6 hours, and then the reaction solution was dropped into diethylether. The resultant precipitation was then collected. The resultant polymer compound was measured by $^1$H-NMR in a solution of heavy ethanol, and then the composition ratio of this polymer compound was calculated from integral values of a peak appeared around 3.4 ppm and assigned to the terminal methoxy group of PEGMA, peaks appeared around 7.6 ppm and 8.4 ppm and assigned to the benzene ring of MEONP, and a peak appeared around 0.7 ppm and assigned to the methylene bonded to Si in MPTMS. The results are shown in Table 1.

Synthesis Example 2 of Polymer Compound

In the same way as in Synthesis Example 1 of the polymer compound, polyethylene glycol methyl ether methacrylate having a number-average molecular weight Mn of about 2080 (also known as methoxypolyethylene glycol methacrylate, which will be referred to as PEGMA2080 hereinafter; a 50% by weight solution thereof in water, available from Aldrich Co., was dehydrated and used), and p-nitrophenyloxycarbonyl-polyethylene glycol methacrylate (hereinafter referred to as MEONP) were dissolved in dehydrated ethanol, so as to prepare a monomer mixed solution. The total concentration of the monomers was 0.2 mol/L. About the mol ratio between the individual monomers, the ratio of PEGMA2080 to MEONP was 85 to 15. Furthermore, thereto were added (3-mercaptopropyl)trimethoxysilane (hereinafter referred to as MPTMS and available from Aldrich Co.) and 2,2-azobisisobutyronitrile (hereinafter referred to as AIBN and available from Wako Pure Chemical Industries, Ltd.) so as to set the concentration of each of these components to 0.003 mol/L. The solution was stirred until the solution turned into a homogeneous state. Thereafter, in the atmosphere of argon gas, the reactive components were caused to react at 60° C. for 6 hours, and then the reaction solution was dropped into diethylether. The resultant precipitation was then collected. The resultant polymer compound was measured by $^1$H-NMR in a solution of heavy ethanol, and then the composition ratio of this polymer compound was calculated from integral values of a peak appeared around 3.4 ppm and assigned to the terminal methoxy group of PEGMA, peaks appeared around 7.6 ppm and 8.4 ppm and assigned to the benzene ring of MEONP, and a peak appeared around 0.7 ppm and assigned to the methylene bonded to Si in MPTMS. The results are shown in Table 1.

Synthesis Example 3 of Polymer Compound

A polymer compound was obtained in the same way as in Synthesis Example 1 except that (3-mercaptopropyl)dimethylethoxysilane (hereinafter referred to as MPDES) was used instead of (3-mercaptopropyl)trimethoxysilane (referred to as MPTMS hereinafter and available form Aldrich Co.) used in Synthesis Example 1. The composition ratio of the polymer compound was calculated in the same way as described above. The results are shown in Table 1.

Synthesis Example 4 of Polymer Compound

A polymer compound was obtained in the same way as in Synthesis Example 2 except that MPDES was used instead of MPTMS used in Synthesis Example 2. The composition ratio of the polymer compound was calculated in the same way as described above. The results are shown in Table 1.

TABLE 1

|  |  | Synthesis Example 1 | Synthesis Example 2 | Synthesis Example 3 | Synthesis Example 4 |
|---|---|---|---|---|---|
| Charged Composition Ratio | PEGMA1100 | 85 | 0 | 85 | 0 |
|  | PEGMA2080 | 0 | 85 | 0 | 85 |
|  | MEONP | 15 | 15 | 15 | 15 |
| Composition Ratio obtained from 1H-NMR | PEGMA1100 | 87 | 0 | 87 | 0 |
|  | PEGMA2080 | 0 | 83 | 0 | 86 |
|  | MEONP | 13 | 15 | 13 | 13 |
|  | MPTMS | 0.5 | 1.9 |  |  |
|  | MPDES |  |  | 0.7 | 0.6 |

Unit: mol ratio

Example 1 to 4

A saturated cyclic polyolefin resin (a hydrogenated ring-opening polymerized product of 5-methyl-2-norbornene (MFR (melt flow rate): 21 g/10-min., hydrogenation ratio: substantially 100%, thermal deformation temperature: 123° C.) was formed into a slide glass shape (dimension: 76 mm×26 mm×1 mm) by injection molding, so as to form a solid phase substrate. The surfaces of the substrate were subjected to oxidizing treatment by plasma treatment in the atmosphere of oxygen. This solid phase substrate was dipped into a 1.0% by weight ethanol solution of each polymer compounds obtained by the Synthesis Examples 1 to 4, thereby introducing, onto the surfaces of the substrate, a layer containing a polymer compound which was a copolymer containing repeating units derived from the ethylenically unsaturated polymerizable monomer (a) having an alkylene glycol residue and the ethylenically unsaturated polymerizable monomer (b) having a functional group for fixing a biologically active substance, this copolymer having, on at least one terminal side thereof, an alkoxyl group. This substrate was heated and dried at 100° C. for 2 hours, thereby bonding the substrate and the polymer-containing layer chemically.

Comparative Example 1

Non-Coated Substrate

A saturated cyclic polyolefin resin (a hydrogenated ring-opening polymerized product of 5-methyl-2-norbornene (MFR (melt flow rate): 21 g/10-min., hydrogenation ratio: substantially 100%, thermal deformation temperature: 123° C.) was formed into a slide glass shape (dimension: 76 mm×26 mm×1 mm) by injection molding, so as to form solid phase substrates. The surfaces of the substrates were subjected to oxidizing treatment by plasma treatment in the atmosphere of oxygen.

Comparative Example 2

Aldehyde-Coated Substrate

A saturated cyclic polyolefin resin (a hydrogenated ring-opening polymerized product of 5-methyl-2-norbornene (MFR (melt flow rate): 21 g/10-min., hydrogenation ratio: substantially 100%, thermal deformation temperature: 123° C.) was formed into a slide glass shape (dimension: 76 mm×26 mm×1 mm) by injection molding, so as to form a solid phase substrate. The surfaces of the substrate were subjected to oxidizing treatment by plasma treatment in the atmosphere of oxygen. This substrate was dipped into a 2% by volume ethanol solution of 3-aminopropyltrimethoxysilane. Thereafter, the substrate was washed with pure water, and then thermally treated at 45° C. for 2 hours, thereby introducing amino groups thereto. Furthermore, the substrate was dipped into a 1% by volume aqueous solution of glutaraldehyde, and then washed with pure water, thereby introducing aldehyde groups thereto.

Comparative Example 3

An amine-reactive slide glass substrate was formed in accordance with Example X in Patent Document 2 (Japanese Patent Application National Publication (Laid-Open) No. 2004-531390).

Specifically, a coating solution was first prepared as follows:

<Preparation of Coating Solution>

In a vial of polypropylene, 26.5 µL of (3-trimethoxysilyl-propyl)-diethylenetriamine (Gelest Inc.) was added to 10 mL of an organic solvent to prepare a solution of an aminosilane in the organic solvent. As the solvent, dimethylsulfoxide (DMSO) or N,N-dimethylacetoamide (DMAC), each of which is commercially available from Aldrich Co., can be used. Next, 1.0 mL of this solution was added to 40 mg of biotin-PEG-SPA (manufactured by Shearwater Polymer, Inc.; SPA is a succinimidyl derivative of propionic acid, which exhibits reactivity with an amine group). The SPA group of biotin-PEG-SPA reacts with the terminal amine of the aminosilane to produce a biotin-PEG-silane molecule. The biotin-PEG-silane/DMAC solution is called a solution A.

In another vial, 70.6 µL of 6-azidesulfonylhexyl-triethoxy-sialne was added to 10 mL of DMSO. To this solution was added 125 µL of a matrix-forming solution (polyoxyethylene sorbitan tetraoleate, Aldrich) to obtain a solution B. The solution A and the solution B were mixed at a ratio by volume of 1 to 4 (1 mL of the solution A was added to 4 mL of the solution B) to obtain a coating solution mixture.

Next, a slide glass, 25×75 mm, for a microscope was coated with an approximate 400 angstroms radio frequency sputtered silicon oxide layer and then cleaned the following protocol. The slide glass was first rinsed with high purity water; the slide glass was loaded in a glass staining rack, and this was dipped into a degassed 1% ALCONOX solution (an alkaline glass cleaner) of 60° C. temperature; the slide glass was then subjected to ultrasonic treatment for 15 minutes; next, the slide glass was rinsed with a large amount of high purity water, and further subjected to ultrasonic treatment in high purity water of 60° C. temperature; and next the slide glass was rinsed with a large amount of high purity water, and then placed in fresh ultra pure water until the glass was supplied to a drying step. The slide glass was sufficiently blown dry with compressed $N_2$ gas and was stored in the dry state until use. The cleaned and pre-treated slide glass was mounted in a spin coater, and then rotated at 3500 rpm. Onto the pre-treated slide glass was supplied 0.5 mL of a fraction from the coating solution mixture, and then the glass was rotated for 90 seconds.

The coated slide glass, 25×75 mm, was placed in a vacuum oven, and subsequently the pressure therein was reduced to a pressure of 150 mmHg for 30 minutes. The oven was switched on so as to heat the slide glass up to about 70° C. The total time for the treatment for the heating (the heating inclination, and the maintenance of the heating) was 1 hour. Next, the substrate was naturally cooled to room temperature in ambient air.

Experiment 1

Each of the substrates obtained in Examples and Comparative Examples was evaluated as follows: about the substrates of Examples 1 to 4 and the substrate of Comparative Example 3, an experiment described below was repeated 5 times to check the reproducibility. The reproducibility was evaluated in a system to which mouse IgG2a as an antigen was not added.

Process 1 (Fixation of Primary Antibody)

A sandwich method was conducted on each of the substrates obtained in Examples and Comparative Examples. Specifically, a primary antigen, anti-mouse IgG2a prepared into a concentration of 3.3 µmol/L with a carbonate buffer (available from Wako Pure Chemical Industries, Ltd.; pH: 9.5) was first spotted onto each of the substrates by means of an automatic spotter. Thereafter, the resultant was allowed to stand still at room temperature for 24 hours, thereby fixing the primary antibody.

Process 2 (Adsorption Preventing Treatment)

Thereafter, each of the substrates of Examples 1 to 4 was dipped into an aqueous solution (pH: 9.5) composed of 0.1 mol/L ethanolamine (available from Wako Pure Chemical Industries, Ltd.; ultra pure grade) and a 0.1 mol/L solution of tris buffer (manufactured by SIGMA) in water (ratio by volume: 1/1) for 1 hour so as to inactivate the remaining active ester groups. Moreover, one of the substrates of Comparative Example 1 was subjected to the adsorption preventing treatment by dipping, for 2 hours, into a solution obtained by diluting a commercially available adsorption preventing agent, "BLOCK ACE" (manufactured by Dainippon Pharmaceutical Co., Ltd.) 4 times with a PBS buffer (manufactured by Nissui Pharmaceutical Co., Ltd.: a buffer wherein 9.6 g of tissue-culturing Dulbecco PBS(-) was dissolved in 1 L of pure water). The other substrate of Comparative Example 1 was not subjected to any adsorption preventing treatment. The substrate of Comparative Example 2 was subjected to the adsorption preventing treatment by dipping, for 2 hours, into a solution obtained by diluting a commercially available adsorption preventing agent, "BLOCK ACE" (manufactured by Dainippon Pharmaceutical Co., Ltd.) 4 times in the same way as described above.

Process 3 (Antigen-Antibody Reaction 1)

Thereafter, an FBS (fetal bovine serum) solution was prepared by diluting to 10% with a PBS buffer (manufactured by Nissui Pharmaceutical Co., Ltd.: a buffer wherein 9.6 g of tissue-culturing Dulbecco PBS(-) was dissolved in 1 L of pure water). To this solution was added the mouse IgG2a as the antigen to produce a solution wherein the concentration thereof was 20 nmol/L. This solution was diluted with an FBS (fetal bovine serum) solution diluted into 10% with a PBS buffer (manufactured by Nissui Pharmaceutical Co., Ltd.: a buffer wherein 9.6 g of tissue-culturing Dulbecco PBS(-) was dissolved in 1 L of pure water) one time, 2 times, 3 times, and 4 times, respectively, so as to yield diluted solutions. These diluted solutions, and a 10% FBS solution containing no antigen IgG 2a were each brought into contact with each of the substrates at 37° C. for 2 hours, thereby conducting antigen-antibody reaction. After the antigen-antibody reaction, the resultant was washed with a 1×SSC buffer (obtained by diluting SSC20× Buffer manufactured by Zymed Laboratories, Inc.), to which a 0.05% by weight nonionic surfactant Tween 20 (manufactured by Roche Diagnostics K.K.) was added, at room temperature for 5 minutes.

Process 4 (Antigen-Antibody Reaction 2)

After washed, a biotin-labeled anti-mouse IgG2a as a second antibody was added to a PBS buffer (manufactured by Nissui Pharmaceutical Co., Ltd.: a buffer wherein 9.6 g of tissue-culturing Dulbecco PBS (-) was dissolved in 1 L of pure water), thereby preparing a solution wherein the concentration thereof was 20 nmol/L. Antigen-antibody reactions were conducted by bringing each substrate into contact with this solution at 37° C. for 2 hours. After the antigen-antibody reaction, the resultant was washed with a 1×SSC buffer (obtained by diluting SSC20× Buffer manufactured by Zymed Laboratories, Inc.), to which a 0.05% by weight nonionic surfactant Tween 20 (manufactured by Roche Diagnostics K.K.) was added, at room temperature for 5 minutes.

Process 5 (Labeling)

At last, Cy5-labeled streptavidin was added to a PBS buffer (manufactured by Nissui Pharmaceutical Co., Ltd.: a buffer wherein 9.6 g of tissue-culturing Dulbecco PBS(-) was dissolved in 1 L of pure water), thereby preparing a solution wherein the concentration thereof was 20 nmol/L. This solution and each of the substrates were brought into contact with each other at 37° C. for 30 minutes to cause reaction, and then the resultant was washed with a 1×SSC buffer (obtained by diluting SSC20× Buffer manufactured by Zymed Laboratories, Inc.), to which a 0.05% by weight nonionic surfactant Tween 20 (manufactured by Roche Diagnostics K.K.), at room temperature for 5 minutes, thereby labeling the substrate.

About each of the substrates, fluorescent amount measurement was conducted, and then the spot signal intensity value and the background value thereof were evaluated. The results of the background values are shown in Table 2, the results of the spot signal intensities are shown in Table 3, and the results of the reproducibility test are shown in Table 4.

In the measurement of the fluorescent amounts in Examples and Comparative Examples, a microarray scanner "Scan Array" manufactured by Packard BioChip Technologies Co. was used. Conditions for the measurement were as follows: the laser power was 90%, the PMT sensitivity was 50%, the excitation wavelength was 649 nm, the measurement wavelength was 670 nm, and the resolution was 50 µm.

By comparing Examples 1 to 4 with Comparative Example 1 treated with no BLOCK ACE, it has been verified that according to the biochip substrate of the invention the background value is reduced.

By comparing Examples 1 to 4 with Comparative Example 2, it has been understood that the biochip substrate according to the invention have the lower background values and the higher signal intensity values, in comparison with a case that a conventional aldehyde substrate was treated with a commercially available adsorption preventing agent.

By comparing Examples 1 to 4 with Comparative Example 3, it has been understood that: the biochip substrates according to the present invention have the lower background values than that of the substrate according to Patent Document 2, specifically, the substrate of the invention less adsorbs nonspecific proteins contained in a blood serum; and the biochip substrates according to the present invention have the lower signal intensity value of the primary antibody spotted sites when the sites have no antigen, specifically, the biochip substrate of the invention is a biochip substrate onto which a primary antibody is fixed in the state that the primary antibody keeps the antibody function thereof. Moreover, it has been understood that the biochip substrate according to the invention is a biochip substrate which is also excellent in reproducibility.

TABLE 2

| | Background Value | |
|---|---|---|
| | Block Ace Treatment | Background Value |
| Example 1 | | 723 |
| Example 2 | | 774 |
| Example 3 | | 701 |
| Example 4 | | 682 |
| Comparative Example 1 | Treated | 6,637 |
| Comparative Example 1 | Not treated | 23,426 |
| Comparative Example 2 | Treated | 3,109 |
| Comparative Example 3 | | 1899 |

TABLE 3

| | | Signal Intensity Value | | | | |
|---|---|---|---|---|---|---|
| | | Dilution Factor | | | | |
| | Block Ace Treatment | 1 | 2 | 3 | 4 | Without Antigen |
| Example 1 | | 29,206 | 15,402 | 8,923 | 6,142 | 801 |
| Example 2 | | 28,408 | 14,941 | 8,471 | 6,082 | 939 |
| Example 3 | | 27,021 | 13,992 | 9,919 | 5,023 | 772 |
| Example 4 | | 26,421 | 13,802 | 8,537 | 5,920 | 721 |
| Comparative Example 1 | Treated | 18,439 | 14,279 | 11,453 | 8,145 | 9,721 |
| Comparative Example 1 | Not treated | Not detectable | Not detectable | Not detectable | Not detectable | Not detectable |
| Comparative Example 2 | Treated | 14,211 | 11,427 | 6,727 | 4,873 | 3,437 |
| Comparative Example 3 | | 15,625 | 8,886 | 4,821 | 2,937 | 4,262 |

TABLE 4

| | | Reproducibility (without antigen) | | | | |
|---|---|---|---|---|---|---|
| | | $1^{st}$ | $2^{nd}$ | $3^{rd}$ | $4^{th}$ | $5^{th}$ |
| Example 1 | Background Value | 723 | 732 | 882 | 651 | 774 |
| | Signal Intensity Value | 852 | 823 | 840 | 752 | 842 |
| Example 2 | Background Value | 774 | 829 | 882 | 852 | 899 |
| | Signal Intensity Value | 939 | 921 | 945 | 947 | 953 |
| Example 3 | Background Value | 701 | 802 | 752 | 649 | 711 |
| | Signal Intensity Value | 772 | 782 | 743 | 755 | 751 |
| Example 4 | Background Value | 682 | 703 | 732 | 697 | 732 |
| | Signal Intensity Value | 721 | 778 | 783 | 733 | 796 |
| Comparative Example 3 | Background Value | 1,389 | 2,243 | 1,429 | 2,239 | 1,834 |
| | Signal Intensity Value | 4,262 | 4,437 | 3,905 | 4,945 | 5,495 |

The invention claimed is:

1. A polymer compound for medical material which is a polymer comprising repeating units derived from an ethylenically unsaturated polymerizable monomer (a) having a functional group for fixing a biologically active substance,
    wherein the polymer has a reactive functional group which has a structure represented by the following general formula [4'] on at least one terminal side thereof;
    wherein the polymer is dissolved at a concentration of 0.05 to 10% by weight in a single solvent selected from ethanol, methanol, t-butyl alcohol, benzene, toluene, tetrahydrofuran, dioxane, dichloromethane, chloroform, acetone or methyl ethyl ketone or a mixed solvent thereof:

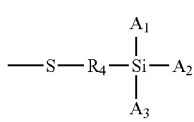

[Formula 4']

wherein at least one of $A_1$, $A_2$ and $A_3$ is a reacive moiety, selected from the group consisting of an alkoxyl group, a halogen group, an amino group, an isocyanate group, a phenoxy group and a hydroxyl group, the remainder of $A_1$, $A_2$, and $A_3$ are each an alkyl group; and wherein $R_4$ is an alkyl group having 1 to 20 carbon atoms,
    and
    wherein the functional group of the ethylenically unsaturated polymerizable monomer (a) having a functional group for fixing a biologically active substance is at least one functional group selected from an aldehyde group, an active ester group, an epoxy group, a vinylsulfone group, and biotin.

2. A polymer compound for medical material according to claim 1, wherein the polymer is a copolymer comprising repeating units derived from an ethylenically unsaturated polymerizable monomer (a) having a functional group for fixing a biologically active substance, and an ethylenically unsaturated polymerizable monomer (b) having an alkylene glycol residue, wherein the copolymer has a structure represented by the general formula [4'] on at least one terminal side thereof, and wherein the copolymer is dissolved at a concentration of 0.05 to 10% by weight in a single solvent selected from ethanol, methanol, t-butyl alcohol, benzene, toluene, tetrahydrofuran, dioxane, dichoromethane, chloroform, acetone or methyl ethyl ketone or a mixed solvent thereof.

3. A polymer compound for medical material according to claim 1, wherein the polymer is a copolymer comprising repeating units derived from an ethylenically unsaturated polymerizable monomer (a) having a functional group for fixing a biologically active substance, an ethylenically unsaturated polymerizable monomer (b) having an alkylene glycol residue, and an ethylenically unsaturated polymerizable monomer (c) having a hydrophobic unit, wherein the polymer has a structure represented by the general formula [4'] on at least one terminal side thereof, and the copolymer is dissolved at a concentration of 0.05 to 10% by weight in a single solvent selected from ethanol, methanol, t-butyl alcohol, benzene, toluene, tetrahydrofuran, dioxane, dichoromethane, chloroform, acetone or methyl ethyl ketone or a mixed solvent thereof.

4. The polymer compound for medical material according to claim 1, wherein the ethylenically unsaturated polymerizable monomer (a) having a functional group for fixing a biologically active substance is a monomer having an active ester group and represented by the following general formula [1]:

[Formula 1]

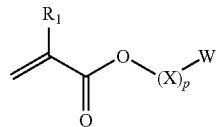

[1]

wherein $R_1$ represents a hydrogen atom or a methyl group, X represents an alkyl group or an alkylene glycol residue having 1 to 10 carbon atoms, W represents an active ester group, and p represents an integer from 1 to 100 provided that when p is an integer of 2 or more and 100 or less, the repeated Xs may be the same or different.

5. The polymer compound for medical material according to claim 1, wherein the active ester group is a p-nitrophenyl ester or N-hydroxysuccinimide ester.

6. The polymer compound for medical material according to claim 2, wherein the ethylenically unsaturated polymerizable monomer (b) having an alkylene glycol residue is a monomer represented by the following general formula [2]:

[Formula 2]

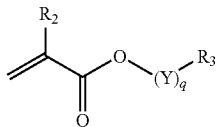

[2]

wherein $R_2$ represents a hydrogen atom or a methyl group, $R_3$ represents a hydrogen atom or an alkyl group having 1 to 20 carbon atoms, Y represents an alkylene glycol residue having 1 to 10 carbon atoms, and q represents an integer from 1 to 100 provided that when q is an integer of 2 or more and 100 or less, the repeated Yq may be the same or different.

7. The polymer compound for medical material according to claim 2, wherein the ethylenically unsaturated polymerizable monomer (b) having an alkylene glycol residue is methoxypolyethylene glycol(meth)acrylate or ethoxypolyethylene glycol(meth)acrylate.

8. The polymer compound for medical material according to claim 7, wherein an average repeating number of the ethylene glycol residue of the methoxypolyethylene glycol (meth)acrylate or ethoxypolyethylene glycol(meth)acrylate is from 3 to 100.

9. The polymer compound for medical material according to claim 3, wherein the hydrophobic group of the ethylenically unsaturated polymerizable monomer (c) having a hydrophobic group is an alkyl group.

10. The polymer compound for medical material according to claim 3, wherein the hydrophobic group of the ethylenically unsaturated polymerizable monomer (c) having a hydrophobic group is n-butyl (meth)acrylate, iso-butyl (meth)acrylate, sec-butyl (meth)acrylate, t-butyl (meth)acrylate, n-neopentyl(meth)acrylate, iso-neopentyl(meth)acrylate, sec-neopentyl(meth)acrylate, neopentyl(meth)acrylate, n-hexyl(meth)acrylate, iso-hexyl(meth)acrylate, heptyl (meth)acrylate, n-octyl(meth)acrylate, iso-octyl(meth)acrylate, 2-ethylhexyl(meth)acrylate, n-nonyl(meth)acrylate, iso-nonyl(meth)acrylate, n-decyl(meth)acrylate, iso-decyl(meth)acrylate, n-dodecyl(meth)acrylate, iso-dodecyl(meth)acrylate, n-tridecyl(meth)acrylate, iso-tridecyl(meth)acrylate, n-tetradecyl(meth)acrylate, iso-tetradecyl(meth)acrylate, n-pentadecyl(meth)acrylate, iso-pentadecyl(meth)acrylate, n-hexadecyl(meth)acrylate, iso-hexadecyl(meth)acrylate, n-octadecyl(meth)acrylate, iso-octadecyl(meth)acrylate, cyclohexyl(meth)acrylate, or isobornyl(meth)acrylate.

11. The polymer compound for medical material according to claim 3, wherein the ethylenically unsaturated polymerizable monomer (c) having a hydrophobic group is at least one monomer selected from n-butyl methacrylate, n-dodecyl methacrylate, n-octyl methacrylate, and cyclohexyl methacrylate.

12. A process for producing a polymer compound for medical material defined by claim 1, wherein at least an ethylenically unsaturated polymerizable monomer (a) having a functional group for fixing a biologically active substance is subjected to radical polymerization in the presence of a mercapto compound (d) having a reactive functional group to obtain the polymer compound having the reactive functional group introduced to the terminal thereof.

13. A process for producing a polymer compound for medical material according to claim 12, wherein at least an ethylenically unsaturated polymerizable monomer (a) having a functional group for fixing a biologically active substance and an ethylenically unsaturated polymerizable monomer (b) having an alkylene glycol residue are subjected to radical copolymerization in the presence of a mercapto compound (d) having a reactive functional group to obtain the polymer compound having the reactive functional group introduced to the terminal thereof.

14. The process for producing a polymer compound for medical material according to claim 12, wherein the mercapto compound (d) having a reactive functional group is a mercaptosilane compound represented by the following general formula [3]:

[Formula 3]

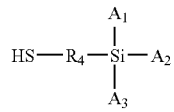

[3]

wherein $R_4$ represents the alkyl group having 1 to 20 carbon atoms, and at least one of $A_1$, $A_2$ and $A_3$ is the reactive moiety, and the remainder of $A_1$, $A_2$, and $A_3$ are each the alkyl groups.

15. The process for producing a polymer compound for medical material according to claim 14, wherein the reactive moiety of the mercaptosilane compound represented by the general formula [3] is an alkoxyl group.

16. A surface coating material for medical material, which comprises the polymer compound for medical material defined by claim 1.

17. A biochip substrate, wherein a layer comprising a surface coating material for medical material according to claim 16 is formed on a surface of a substrate.

18. The biochip substrate according to claim 17, wherein the substrate is made of a plastic.

19. The biochip substrate according to claim 18, wherein the plastic is a saturated cyclic polyolefin.

20. A biochip, wherein a biologically active substance is fixed to a biochip substrate according to claim 17.

21. The biochip according to claim 20, wherein the biologically active substance is at least one biologically active substance selected from nucleic acid, aptamer, protein, oligopeptide, sugar chain and glycoprotein.

22. The polymer compound for medical material according to claim 1, wherein the general compound is derived from (3-mercaptopropyl)trimethoxysilane, (3-mercaptopropyl)methyldimethoxysilane, (3-mercaptopropyl)dimethylmethoxysilane, (3-mercaptopropyl)triethoxysilane, (3-mercaptopropyl)methyldiethoxysilane, (3-mercaptopropyl)dimethylethoxysilane, (mercaptomethyl)trimethoxysilane, (mercaptomethyl)methyldimethoxysilane, (mercaptomethyl)dimethylmethoxysilane, (mercaptomethyl)triethoxysilane, (mercaptomethyl)methyldiethoxysilane, (mercaptopropyl)dimethylethoxysilane, or mixtures thereof.

23. The polymer compound for medical material according to claim 22, wherein the general compound is derived from (3-mercaptopropyl)trimethoxysilane or (3-mercaptopropyl)triethoxysilane.

24. The polymer compound for medical material according to claim 22, wherein the general compound is derived from (3-mercaptopropyl)dimethylethoxysilane.

* * * * *